United States Patent
Bunquin et al.

(10) Patent No.: US 9,051,229 B2
(45) Date of Patent: *Jun. 9, 2015

(54) TRANSITION METAL CATALYSTS FOR C—O HYDROGENOLYSIS AND HYDRODEOXYGENATION

(71) Applicant: GOVERNORS OF THE UNIVERSITY OF ALBERTA, Alberta (CA)

(72) Inventors: Jeffrey Camacho Bunquin, Alberta (CA); Jeffrey Mark Stryker, Alberta (CA)

(73) Assignee: Governors of the University of Alberta (CA)

( * ) Notice: Subject to any disclaimer, the term of this patent is extended or adjusted under 35 U.S.C. 154(b) by 0 days.

This patent is subject to a terminal disclaimer.

(21) Appl. No.: 13/725,595

(22) Filed: Dec. 21, 2012

(65) Prior Publication Data

US 2014/0179954 A1 Jun. 26, 2014

(51) Int. Cl.

| | | |
|---|---|---|
| C07C 1/22 | (2006.01) | |
| B01J 31/18 | (2006.01) | |
| C07C 1/20 | (2006.01) | |
| C07C 1/247 | (2006.01) | |
| C07B 31/00 | (2006.01) | |
| C07C 37/055 | (2006.01) | |
| C07C 41/26 | (2006.01) | |
| C07C 41/18 | (2006.01) | |

(52) U.S. Cl.
CPC . *C07C 1/22* (2013.01); *C07C 41/18* (2013.01); *C07C 37/055* (2013.01); *C07C 41/26* (2013.01); *C07B 31/00* (2013.01); *C07C 1/20* (2013.01); *C07C 1/247* (2013.01); *C07C 2101/10* (2013.01); *C07C 2101/20* (2013.01); *C07C 2531/12* (2013.01); *C07C 2531/14* (2013.01); *C07C 2531/18* (2013.01); *B01J 31/188* (2013.01); *B01J 2231/64* (2013.01); *B01J 2531/0216* (2013.01); *B01J 2531/842* (2013.01); *B01J 2531/845* (2013.01); *B01J 2531/847* (2013.01)

(58) Field of Classification Search
None
See application file for complete search history.

(56) References Cited

U.S. PATENT DOCUMENTS

| 6,239,061 | B1 | 5/2001 | Wang et al. | |
|---|---|---|---|---|
| 6,300,435 | B1 * | 10/2001 | Gao et al. | 526/133 |
| 6,846,769 | B2 | 1/2005 | Arndt-Rosenau et al. | |

FOREIGN PATENT DOCUMENTS

| CA | 2605077 | 4/2009 |
|---|---|---|
| EP | 0881233 | 12/1998 |
| EP | 0890581 | 1/1999 |
| WO | WO 00/05236 | 2/2000 |
| WO | WO 00/05238 | 2/2000 |
| WO | WO 01/19512 | 3/2001 |
| WO | WO 2009/043156 | 4/2009 |
| WO | WO 2009/043157 | 4/2009 |

OTHER PUBLICATIONS

Dehnicke et al., "Phosphoraneiminato complexes of transition metals," Coordination Chemistry Reviews, 1999, vol. 182, Iss. 1, pp. 19-65.

Guérin et al., "Synthesis, Structure, and Reactivity of the Phosphinimide Complexes $(t\text{-}Bu_3PN)_nMX_{4-n}$ (M=Ti, Zr)," Organometallics, 2000, vol. 19, Iss. 16, pp. 2994-3000.

Klien et al., "Novel Imido- and Phosphorane-Imido-Nickel(II) Complexes. Crystal and Molecular Structure of $(\mu_3\text{-}NH)(\mu_3\text{-}NPMe_3)(NiClPMe_3)_3$," Journal of the American Chemical Society, 1991, vol. 113, pp. 4673-4675.

Mast et al., "Vinyl-type polymerization of norbornene by a nickel-based catalyst with phosphoraneiminato ligands," Macromolecular Rapid Communications, 1999, vol. 20, Iss. 4, pp. 232-235.

Ramos et al., "Titanium ferrocenyl-phosphinimide complexes," Dalton Transactions, 2010, vol. 39, Iss. 5, pp. 1328-1338.

Riese et al., Cobalt(II)-organische Phosphaniminato-Komplexe mit Heterocuban-Struktur. Kristallstrukturen von $[CoBr(NPR_3)]_4$ mit R=Me, Et, $[Co(C\equiv C\text{—}CMe_3)(NPMe3)]_4$ und $[Co(C\equiv C\text{—}SiMe_3)(NPEt_3)]_4$, Zeitschrift für anorganische und allgemeine Chemie (Journal of Inorganic and General Chemistry), 1998, vol. 624, Iss. 8, pp. 1279-1284.

Schroers et al., "Grafting of Vinyl-Type Polynorbornene on Polybutadiene and Polyisoprene," Macromolecular Chemistry and Physics, 2002, vol. 203, Iss. 18, pp. 2658-2664.

Yadav et al., "Phosphinimide complexes with pendant hemilabile donors: synthesis, structure and ethylene polymerization activity," Dalton Transactions, 2009, Iss. 9, pp. 1636-1643.

\* cited by examiner

*Primary Examiner* — Brian J Davis
(74) *Attorney, Agent, or Firm* — Sheridan Ross P.C.

(57) ABSTRACT

Phosphoranimide-metal catalysts and their role in C—O bond hydrogenolysis and hydrodeoxygenation (HDO) are disclosed. The catalysts comprise of first row transition metals such as nickel, cobalt and iron. The catalysts have a metal to anionic phosphoranimide ratio of 1:1 and catalyze C—O bond hydrogenolyses of a range of oxygen-containing organic compounds under lower temperature and pressure conditions than those commonly used in industrial hydrodeoxygenation.

24 Claims, No Drawings

TRANSITION METAL CATALYSTS FOR C—O HYDROGENOLYSIS AND HYDRODEOXYGENATION

FIELD

The disclosure relates to transition metal catalysts and the role of these catalysts in mediating C—O bond hydrogenolysis and hydrodeoxygenation reactions of a range of organic compounds with at least one carbon-oxygen bond. More particularly, the disclosure relates to phosphoranimide-transition metal catalysts having a phosphoranimide to metal ratio of 1:1 and a method of C—O bond hydrogenolysis and hydrodeoxygenation applicable to a range of organic compounds including diaryl ethers, alkyl aryl ethers, furan derivatives, ketones and enones.

BACKGROUND

Cost-effective cleavage of carbon-oxygen bonds plays an important role and remains a great challenge in energy production and fine chemicals synthesis. With the increasing demand for fuel and commodity chemicals and our dependence on non-renewable resources like petroleum, the area of catalysis has recently started to develop practical alternative strategies to produce fuels and commodity chemicals from renewable and terrestrially abundant sources such as oxygen-rich biopolymers, i.e., biomass. Current catalytic processes for the reductive upgrading of biomass employ high temperatures, high pressures and high catalyst loadings, compromising precious and semi-precious transition metals. The inherently high oxygen content of biomass poses refining problems due to coke formation under harsh processing conditions, thus, compromising process efficiencies and profitability. The catalytic reduction of lignocellulose, in particular, has been widely studied using conventional cobalt- and nickel-promoted molybdenum and tungsten catalysts used commercially for petroleum hydrotreatment. The heterogeneous nature of these catalysts results in non-selective oxygen extrusion from these diversely functionalized biopolymers through various competing pathways, ultimately affording complicated mixtures of products at low conversion.

Optimal catalysts for biomass refining are systems that afford high conversion under moderate reaction conditions. Reductive scission of C—O bonds under relatively low temperatures will minimize char formation and other competitive thermal reactions. High selectivity for direct C—O bond hydrogenolysis is desired to suppress excessive hydrogen consumption as most heterogeneous catalysts hydrogenate aromatic rings prior to C—O bond scission, producing cycloalkanes and cycloakanols which are lower value commodity chemicals. Moreover, ideal biomass hydrotreatment catalysts should effect tandem depolymerization and refining to convert bio-oils into higher value liquid fuels via side chain removal.

The development of first row transition metal catalysts for hydrotreatment has not received much attention because such compounds are believed to possess low activity. On the contrary, recent results from credible investigators on the nature of inorganic supports and catalyst concentrations suggest that the active catalytic center in commercial cobalt-molybdenum sulfide ($CoMoS_2$) catalysts may well be the cobalt rather than the molybdenum, as is typically thought. Though most lignocellulose refining strategies in the literature are catalyzed by precious second- and third-row metals, it is important to note that the most efficient upgrading technology thus far, is mediated by an FeS catalyst.

SUMMARY OF THE INVENTION

According to one aspect, there is provided a method of catalyzing a C—O bond hydrogenolysis reaction comprising: reacting an organic substrate having at least one carbon-oxygen bond with a catalyst of general formula:

where:
M is a first row transition metal having a +1 oxidation state;
n is a whole number;
the ratio of M to $R_3PN^-$ in the catalyst is 1:1; —$R_3PN^-$ is a monoanioinic phosphoranimide ligand of structure:

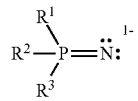

where:
$R^1$, $R^2$, $R^3$ can be the same group or different groups; $R^1$, $R^2$, $R^3$ are independently alkyl (C1-18, primary, secondary or tertiary alkyl), cycloalkyl (C3-C8), aryl/heteroaryl, substituted aryl/heteroaryl or an inert functional group containing at least one heteroatom; and $R^1$, $R^2$, $R^3$ may be linked to give cyclic systems.

In one embodiment, the catalyst has formula $[M(NPR3)]_n$ and n is at least 2. In another embodiment, n is 2 to 8.

According to a second aspect, there is provided a method of catalyzing the C—O bond hydrogenolysis of an organic compound having at least one carbon-oxygen bond comprising: reacting the organic substrate with a catalyst selected from the group consisting of $[Fe(NP^tBu_3)]_4$, $[Co(NP^tBu_3)]_4$ and $[Ni(NP^tBu_3)]_4$.

According to a third aspect, there is provided a method of catalyzing the C—O bond hydrogenolysis of an organic substrate comprising: reacting the organic substrate with a catalyst of Formula $[M(NPR_3)]_n$ wherein n is a whole number; the ratio of M to $NPR_3$ in the catalyst is 1:1;
M is a first row transition metal selected from the group consisting of Fe, Co and Ni;
$NPR_3$ is:

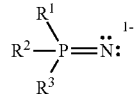

where:
$R^1$, $R^2$, $R^3$ are independently alkyl (C1-18, primary, secondary or tertiary alkyl), cycloalkyl (C3-C8), aryl/heteroaryl, substituted aryl/heteroaryl and an inert functional group containing at least one heteroatom selected from a Group 14, Group 15 and Group 16 element; and wherein $R^1$, $R^2$, $R^3$ may also be linked by aliphatic groups to give cyclic systems; wherein the reaction is carried out at a temperature range of about 50 to 300° C. in the presence of a reducing agent selected from the group consisting of hydrogen and an organic silyl hydride.

According to a fourth aspect, there is provided a process for C—O bond hydrogenolysis of an organic substrate having at least carbon-oxygen bond comprising: (i) combining the said organic substrate with a transition metal complex of Formula II and a reductant selected from hydrogen and an organic silyl hydride to obtain a reaction medium; (ii) allowing the catalyst to catalyze the C—O bond hydrogenolysis of the substrate in an organic substrate selected from toluene and tetrahydrofuran; (iii) obtaining the hydrogenolysis products derived from the organic substrate; wherein the organic substrate is an aromatic or aliphatic compound containing at least one carbon-oxygen bond; and wherein the complex of Formula II is:

where
n is a whole number; the ratio of M to $NPR_3$ in the catalyst is 1:1; M is a first row transition metal selected from the group consisting of Fe, Co and Ni;
$NPR_3$ is:

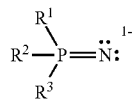

where: $R^1$, $R^2$, $R^3$ are independently alkyl (C1-18, primary, secondary or tertiary alkyl), cycloalkyl (C3-C8), aryl/heteroaryl, substituted aryl/heteroaryl or an inert functional group containing at least one heteroatom selected from the group consisting of a Group 14, Group 15 and Group 16 element; and wherein $R^1$, $R^2$, $R^3$ may also be linked by aliphatic groups to give cyclic systems.

In one embodiment, the catalyst has formula $[M(NPR3)]_n$ and n is at least 2. In another embodiment, n is 2 to 8.

DETAILED DESCRIPTION

The present disclosure relates to homogeneous ligand-supported coordination complexes that function as catalysts for C—O bond hydrogenolysis and HDO reactions. These catalysts of the present disclosure are coordinatively unsaturated. Coordinatively unsaturated catalysts are typically less stable and more reactive than coordinatively saturated catalysts, which makes them candidates for various organic transformations. The catalysts described herein comprise at least one metal having a formal oxidation state of +1 bonded to a monoanionic phosphoranimide ligand, the catalyst typically being in the form of a cluster of metal atoms, with the metal atoms bridged by monoanionic phosphoranimide ligands.

The metal atoms that comprise the catalysts are first row transition metals. The first-row transition metals are supported by anionic phosphoranimide ligands. The catalysts can function under relatively low temperatures (e.g., 100 to 200° C.) and relatively low hydrogen pressures (e.g., 1 atm to about 100 atm) and can catalyze a range of organic transformations, including C—O bond hydrogenolysis and hydrodeoxygenation. These reaction conditions are milder than the reaction conditions typically required by heterogeneous hydrotreatment (HDS, HDO) catalysts. As used herein, the term "mild" used in reference to reaction conditions refers to temperature conditions lower than about 300° C. and pressure conditions of less than about 100 atmospheres. The reaction conditions required for C—O bond hydrogenolysis and hydrodeoxygenation will necessarily vary, being dependent on the catalyst, the substrate and the solvent(s) used, among other factors, and this disclosure is not limited to a particular temperature range and pressure range. It has been observed that the catalysts can function at higher pressures and temperatures than solely the mild conditions just described. Accordingly, in practice, the temperature and pressure range for functionality of the catalysts in quite broad.

The catalysts consist of an assembly of monomeric units having the empirical formula:

$[M(NPR_3)]$  Formula I where:
the ratio of M to $NPR_3$ is 1:1;
M is a first row transition metal;
$NPR_3$ is:

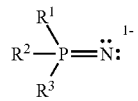

where:
$R^1$, $R^2$, $R^3$ are independently alkyl (C1-18, primary, secondary or tertiary alkyl), cycloalkyl (C3-C8), aryl/heteroaryl, substituted aryl/heteroaryl or an inert functional group containing at least one heteroatom, as defined below and wherein $R^1$, $R^2$, $R^3$ may also be linked by aliphatic groups to give cyclic systems, [(e.g., R1/R2=—$(CH_2)_n$—, where n=3-10].

According to one embodiment, the first row transition metal catalyst may be Fe, Co, Ni or Mn. The Examples below describe catalysts having Fe, Co or Ni as the metal centers. According to one embodiment, the heteroatoms are Group 14, 15 and 16, preferably Si, N or O.

The catalysts of the present disclosure will be referred to, throughout this disclosure, using the following general formula:

$[M(NPR_3)]_n$  Formula II where:
n is a whole number;
M and $NPR_3$ are as defined above for the compound of Formula I.

The $[M(NPR_3)]_n$ complex can adapt various modes of aggregation to form clusters. The present disclosure further discloses catalysts having general formula:

$[M(NPR_3)]_4$  Formula III wherein M, $NPR_3$ are as defined above for the compound of Formula I.

As a specific, non-limiting example, the catalysts of Formula III are discrete tetrametallic transition metal clusters having the following structural formula:

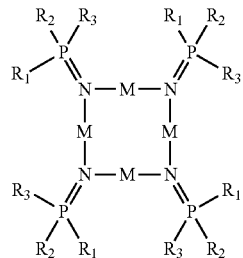

The metal centers of the catalysts of Formula III are supported by bridging, anionic phosphoranimide ligands. Each tetrametallic cluster consists of four nitrogen-bridged phosphoranimidometal(I) (i.e., $MNPR_3$) monomers.

As a person skilled in the art would appreciate, complexes of Formula II can adapt various modes of aggregation. As a result, compounds of Formula II represents a library of catalysts. Structurally characterized compounds of Formula III comprise a subclass of catalysts of Formula II. Compounds of Formula III form an aggregation of four monomeric units of Formula I. Catalysts supported with phosphoranimide ligands of similar electronic and steric properties with, for example, tri-t-butylphosphoranimide may adopt a tetrameric structure. However, unless specifically provided in the Examples, the catalysts of the present disclosure do not represent a particular structure.

Based on the structure of Formula III catalysts, it should be apparent that the phosphoranimide (P=N) functional group displaces R1, R2 and R3 away from the metal center allowing for steric accessibility of the metal center. Thus, the metal center is still active, despite the presence of bulky substituents on the phosphoranimide. Each metal center in the Formula III catalysts may have a coordination number of 2 and an oxidation state of +1. The steric accessibility and low-valent nature of the metal centers result in enhanced activity toward reductive transformations such as HDS, as well as other hydrotreatment reactions.

As a specific example, in the compounds of Formula I, II, III (discussed above) and IV (discussed below), trialkyl- and triarylphosphoranimides can impart thermal stability depending on the phosphorous substituents. Other substituents can be expected to impart similar stability as well, thus providing for the range of catalysts that can be used for the C—O bond hydrogenolysis process described herein.

DEFINITIONS

As used herein, the term "alkyl" includes $C_1$ to $C_{18}$ straight chain, branched or cyclic alkyl groups such as, but not limited to, ethyl, propyl, isopropyl and t-butyl.

As used herein, the term "aryl" includes aromatic hydrocarbons as substituents. Aryl groups may have one or more aromatic rings which may be fused or connected by a connecting group or a bond. Specific examples include, but are not limited to phenyl, tolyl, naphthenyl and biphenyl.

As used herein, the term "heteroaryl" includes aromatic hydrocarbons which contain at least one heteroatom. Similar to the aryl groups, heteroaryls may have one or more aromatic rings which may be fused or connected by a connecting group or a bond.

As used herein, the term "inert functional group" designates heteroatom-bearing hydrocarbyl fragments attached via the heteroatom to aryl and heteroaryl ligand substituents, as defined above, or appended to the terminus of a ligand substituent. The former serve to modulate, electronically and/or sterically, the chemical nature of the phosphoranimide ligand(s), modifying but not impeding catalyst performance. The latter can function as a point of further chemical attachment(s) (i.e., derivatization), for example, in order to construct supported heterogeneous catalysts comprising chemically bonded or linked phosphoranimidometal catalyst subunits grafted onto conventional catalyst supports.

As used herein, the term "heteroatom" is a Group 14, 15 or 16 element, preferably Si, N and O. As used herein, the term "derivative" is a functionalized version of an oxygen-containing substrate where the substituent R's are not all hydrogen.

As used herein, the term "pseudohalide" refers to anions with similar properties to halides preferably $OSO_2R^-$, where R=Me, Ph, p-Tol, $CF_3$.

Reaction Chemistry

The process involves contacting the oxygen-containing substrate with a metal catalyst of general Formula II, $[M(NPR_3)]_n$, as defined above, in the presence of a reducing agent to effect the reductive cleavage of the carbon-oxygen bond(s) in the substrate. In this process, the catalyst breaks the carbon-oxygen bond(s), replacing the oxygen with hydrogen by the action of the reducing agent (vide infra, hydrogen or organic silyl hydride); the oxygen atoms and/or oxygen-containing groups remaining with the catalyst. The reducing agent also acts to convert the oxygen-bound catalyst to its reduced form, generating water and/or alcohols (vide infra,). The products of the C—O bond hydrogenolysis process are hydrocarbons and/or alcohols, such as alkyl and aromatic alcohols, and water. In one example, aromatic hydrocarbons or a mixture of aromatic hydrocarbons and aromatic alcohols can be produced from the catalytic C—O bond hydrogenolysis of diaryl ethers. In another example, dibenzofuran can be hydrodeoxygenated into the corresponding biphenyl compound or a mixture of biphenyl and 2-phenylphenol.

The generalized reaction scheme ("General Reaction 1") is shown below:

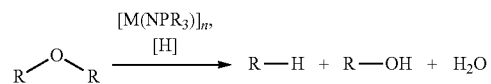

where:
R—O—R is an organic substrate with at least one carbon-oxygen bond;
$[M(NPR_3)]_n$ is a catalyst of Formula II as defined above;
[H] is a chemical reducing agent; R—H is a hydrocarbon product; and
R—OH is an alcohol product.

The present disclosure further describes a process for C—O bond hydrogenolysis wherein a stoichiometric amount of a basic salt is added to scavenge water and/or alcohols produced during the reaction. The following general reaction ("General Reaction 2") describes this process:

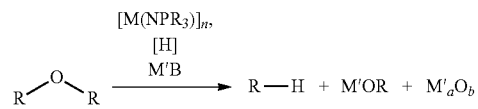

where:
R—O—R is an organic substrate with at least one carbon-oxygen bond;
$[M(NPR_3)]_n$ is a catalyst of Formula II as defined above;
[H] is a chemical reducing agent;
M'B is a basic salt to scavenge $H_2O$;
$M'_aO_b$ is a oxide salt formed from $H_2O$ scavenging, wherein a can be 1 or 2;
b can be 1 or 2;
M'OR is a salt of the alcohol product; and
R—H is hydrocarbon product.

All catalyst loadings where the catalyst to substrate ratio is less than 1:1 can be used for catalytic C—O hydrogenolysis. Generally, the ratio of substrate to catalyst can be much greater than 1000:1 to 1:1, the catalyst being stable under a range of conditions. The catalyst loadings detailed in the Examples range from about 1:375 to 1:15, but these ratios are not the only ratios that can be employed. Suitable catalyst-to-substrate ratios will be dependent on the specific catalyst, concentration, reaction time, and feedstock, among other factors, and can be determined by a person skilled in the art.

The C—O bond hydrogenolysis reactions described above as General Reactions 1 and 2 may be carried out, optionally, in an inert organic solvent. By "inert", it is meant that the solvent does not react with or deactivate the catalyst or interfere in the C—O bond hydrogenolysis process. For example, halogenated solvents such as, but not limited to, dichloromethane ($CH_2Cl_2$) should not be used. Solvents such as toluene, xylene, decalin, methylnaphthalene or tetrahydrofuran (THF) have been used for certain examples. Toluene and THF have been generally used in the examples described herein. In some embodiments, where the oxygen-containing organic substrate is a liquid or low-melting solid, for example, an organic solvent may not be needed in the reaction. Reactions may also be run under triphasic conditions, also called the slurry phase, where some of the substrate, some of the catalyst, or some of each component is not completely dissolved in the selected solvent. The choice of solvent will vary with the properties of the substrate(s) under reduction.

The chemical reducing agent can be hydrogen ($H_2$) or an organic silyl hydride. When the reducing agent is an organic silyl hydride, the silyl hydride may be chosen from the group of phenylsilane, dimethylphenylsilane, ethylsilane or polymeric organosilanes among others. When hydrogen gas is used as the reducing agent, pressures of 1 atm or higher are generally employed. Generally, the reductant is used in an amount sufficient to effectuate the desired level of C—O bond hydrogenolysis. In the case of hydrogen, reactions are routinely run in the presence of a large excess of the reductant, or under conditions of constant hydrogen pressure, wherein the reductant dissolved in the medium is replenished as it is consumed, optimally maintaining a solution saturated in the reductant. In the case of silane, an excess is generally used and no basic scavenger is added to the reduction medium. The silane reacts with the alcohol intermediates and the $H_2O$ by-product to remove the acidic oxygen compounds as they are formed.

In addition, the reaction can be carried out at temperatures ranging from about 50 to 300° C., or greater. The optimal temperature for the reaction will vary depending on the reactor design, reaction scale, solvent(s), reaction time and chemical feedstock. Based on this disclosure, optimum reaction temperature for a particular reaction can be determined by those skilled in the art, but a broad range of reaction temperatures above the low-temperature threshold for conversion is tolerated by the catalysts. The temperature and pressure conditions described herein are milder than those typically employed in industrial hydrotreatment. Accordingly, these catalysts have potential use in industrial processes such as catalytic C—O bond hydrogenolysis and HDO of biomass.

The ratio of the basic metal salts to the oxygen-containing substrate can be greater than or equal to 2:1. The examples provided in this disclosure range from 2:1 to 4:1. The basic metal salts used to scavenge $H_2O$ can be selected from the group consisting of Group I and Group II metal hydrides, but are not limited to these groups. For example, Group I metal hydrides may be LiH, NaH, KH or CsH. Group II metal hydrides can be selected from $MgH_2$ and $CaH_2$. The use of metal hydride scavengers is suitable because the reaction between hydride anions and $H_2O$ to produce $H_2$ gas is irreversible. In addition, the basic metal salts employed in the process can be selected from the group consisting of Group I and Group II salts of strong organic bases, preferably with pKa higher than 20, but are not limited to these organic bases. For example, basic Group I and II salts may be amide salts such as lithium diisopropyl amide (LDA), potassium diisopropylamide (KDA), or Grignard reagents (alkyl or aryl magnesium halides). In some cases, the organo-silyl hydrides may also act as oxygen-scavenger. For example, carvone, an unsaturated ketone, undergoes complete deoxygenation in the presence of stoichiometric amounts phenylsilane (Ph-$SiH_3$), producing a mixture of hydrocarbon products.

In some cases, complete hydrodeoxygenation (HDO) of substrates is achieved in the presence of a Lewis acid additive. For example, dibenzofuran can be completely deoxygenated to biphenyl when trimethylaluminum is present. The Lewis acid co-catalyst can be selected from the group of trialkylaluminum reagents such as trimethylaluminum and triisobutylaluminum. The ratio of the Lewis acid catalyst to the substrate may range from, but not limited to, 1:3 to 1:1.

Purified Catalyst

In one aspect, the process includes the hydrogenolysis of a range of oxygen-containing organic substrates containing at least one carbon-oxygen bond by introducing a "purified" catalyst of Formula II (i.e. $[MNPR_3]_n$) By "purified", it is meant that the catalyst is subjected to purification methods prior to use for catalytic C—O bond hydrogenolysis, as described in the examples provided. The purity may be determined via elemental analysis, for example. In this embodiment, the process involves contacting the organic substrate having at least one carbon-oxygen bond with the metal catalyst of Formula II in the presence of a reducing agent. The reducing agent reacts with the oxygen-containing substrate, converting the carbon-oxygen bonds to carbon-hydrogen bonds. Hydrocarbons or alcohols or a mixture of hydrocarbons and alcohols are produced. The process can be carried out using the reaction conditions described above for General Reactions 1 and 2.

In Situ Catalyst

Another aspect of the present disclosure relates to the use of an in situ-prepared (or in situ-derived) catalyst in C—O bond hydrogenolysis. By "in situ", it is meant that the catalyst is not subject to purification after synthesis. In this embodiment, the catalyst of Formula II $[M(NPR_3)]_n$ is synthesized in situ and used for C—O bond hydrogenolysis directly, without isolation or purification. The in situ-derived catalyst is thus produced through the reduction of metal-phosphoranimide complexes (General Reaction II) having the general formula:

$$[M(NPR_3)X_{(m-1)}]_n \qquad \text{Formula IV}$$

where:
m=2 or 3;
n=2 to 4;
the M to $R_3PN^-$ ratio is 1:1;
M is a first row transition metal;
$X^-$ can be any halide or pseudohalide;
$R^1$, $R^2$, $R^3$ can be the same group or different groups;
$R^1$, $R^2$, $R^3$=alkyl (C1-18, primary, secondary and tertiary alkyl), cycloalkyl (C3-C8), aryl/heteroaryl, substituted aryl/heteroaryl or an inert functional group optionally containing at least one heteroatom; and
$R^1$, $R^2$, $R^3$ substituents may also be linked by aliphatic hydrocarbyl groups to give cyclic systems [(e.g., R1/R2=—$(CH_2)_n$—, where n=3-10].

In one embodiment, the first row transition metal may be Co, Ni, Mn or Fe. In the Examples, Co, Ni and Fe have been found to be suitable.

In one embodiment, the halide may be $F^-$, $Cl^-$, $Br^-$, or $I^-$, and the term "pseudohalide" refers to anions with similar properties to halides preferably $OSO_2R^-$, where R=Me, Ph, p-Tol, $CF_3$.

The present disclosure provides a method for the in situ synthesis of the metal complexes of Formula II [M(NPR$_3$)]$_n$ through the reduction of halide-containing metal phosphoranimide complexes of Formula IV [MNPR$_3$X$_{(m-1)}$]$_n$. The in-situ preparation of the catalyst of Formula II is carried out by treating a complex of Formula IV with an appropriate amount of a chemical reducing agent. The synthesis of this in situ-derived catalyst is conducted as shown below:

General Reaction III

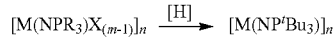

where:

[M(NPR$_3$)X$_{(m-1)}$]$_n$ is a halide-functionalized metal-phosphoranimide complex of Formula IV as defined above;

[H] is a reducing agent;

[M(NPR$_3$)]$_n$ is the metal-phosphoranimide catalyst of Formula II as defined above;

"Chemical reducing agents" are reagents used in two classes of reactions described herein: (1) The chemical reducing agents required to effect the hydrogenolysis of oxygen-containing substrates include hydrogen (H$_2$) or an organic silyl hydride; (2) the chemical reducing agents used for the in situ-synthesis of the catalyst of Formula II [M(NPR$_3$)]$_n$ may be a metal such as but not limited to, Li, Na, or K. It should also be apparent to a person skilled in the art that metal reducing agents may exist in various compounded forms such as, but not limited to, sodium naphthalenide, Na(Hg) amalgam, Na—K alloy, or KC$_8$.

The reduction step can be carried out in inert organic solvents such as tetrahydrofuran, hexane, benzene, diethyl ether or toluene, for example. However, halogen-containing solvents, such as CH$_2$Cl$_2$, for example, are generally unsuccessful in this reduction step.

The ratio of the reducing agent to the total amount of M in the complex of Formula IV [M(NPR$_3$)X$_{(m-1)}$]$_n$ may vary depending on the reducing agent. For example, when the reducing agent is Na(Hg) amalgam, the ratio of the reducing agent to complex with Formula III can range from, but is not limited to, 1:1 to 2:1. Ratios higher than this can be also used for the reduction, but are not necessary. The reduction may be carried out in solvents selected from the group of, but not limited to, tetrahydrofuran, dialkyl ethers, toluene and saturated hydrocarbons such as pentane and hexane.

The reduction step can be conducted at low to ambient temperatures. By "low", it is meant temperatures below about 0° C. and by "ambient", it is meant about normal room temperature. The preferred temperature for the reduction step varies with the complex of Formula IV, the solvent used the concentrations of the various components, and the choice of reducing agent. A person skilled in the art would be able to determine the appropriate reaction temperature. For example, temperatures may range from about −80 to 25° C., when the reaction is carried out in an inert organic solvent. As a specific but non-limiting example, the reduction of [Cl$_2$Co$_2$(μ-NP$^t$Bu$_3$)$_2$(THF)$_2$] using 1% Na(Hg) amalgam, producing [Co(NP$^t$Bu$_3$)]$_4$, may be carried out at about −35° C.

The solution from the reduction process, containing the in situ-derived catalyst, [MNPR$_3$]$_n$, is directly used for C—O bond hydrogenolysis without carrying out the purification procedures described in the synthesis of thoroughly characterized and purified catalyst of Formula II (i.e. [MNPR$_3$]$_n$) and in the synthesis of the unit of Formula I (i.e. [MNPR$_3$]).

The in situ-derived or unpurified catalyst cleaves C—O bonds in organic substrates with at least one carbon-oxygen bond under the same reaction conditions described for General Reactions 1 and II using the purified catalysts of Formula II [MNPR$_3$]$_n$, respectively. The process pertains to contacting an organic molecule with at least one carbon-oxygen bond with the in situ-derived catalyst in the presence of a reducing agent. The reducing agent reacts with the oxygen-containing substrate, thereby converting all or some of the carbon-oxygen bonds to carbon-hydrogen bonds. Hydrocarbons or a mixture of hydrocarbons and alcohols are produced. The process can be conducted optionally in the presence of an inert organic solvent as described above using "purified catalysts" for C—O bond hydrogenolysis.

In another aspect, there is disclosed a method for the synthesis of the in-situ-derived catalyst of Formula II (i.e. [M(NPR$_3$)]$_n$) from an anionic metathesis reaction between a metal halide (MX$_m$) and an alkali or alkaline metal salt of a phosphoranimide ligand, followed directly by the reduction of this intermediate, as described above. The metal precursor can be a metal salt such as MX$_m$ or a solvated metal salt such as L$_a$MX$_m$. This reaction is as illustrated below:

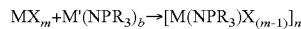

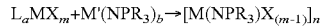

where:

M'(NPR$_3$)$_b$ is a Group I or Group II metal phosphoranimide salt and wherein the anionic phosphoranimide R$_3$PN— ligand is as defined above.

m=2 to 3;

n=1 to 4;

a=1 to 3;

b=1 or 3;

M to R$_3$PN$^-$ ratio in the complex of formula [M(NPR$_3$)X$_{(m-1)}$]$_n$ is 1:1;

M can be any first row transition metals;

X$^-$ can be any halide or pseudohalide;

L can be a two-electron dative donor molecule selected from the group of dialkyl ethers such as, but not limited to, tetrahydrofuran, 1,2-dimethoxyethane, dioxane; or selected from the group of trialkylphosphine and a triarylphosphine such as, but not limited to triphenylphosphine or tri-(p-tolyl) phosphine.

M' can be an alkali or alkaline metal. Alkali phosphoranimide salts (i.e. M'(NPR$_3$)$_b$) employed in the synthesis can include monophosphoranimide salts of lithium, sodium, potassium, and cesium; and alkaline earth metal phosphoranimide salts can include [Mg(NPR$_3$)$_2$] and [Mg(NPR$_3$)X].

The halide may be F$^-$, Cl$^-$, Br$^-$, I$^-$ and the pseudohalide may be OSO$_2$R$^-$ (R=Me, Ph, p-Tol, CF$_3$), for example.

The transition metal may be Mn, Ni, Co, or Fe, for example. In the Examples, Ni, Co and Fe are shown to be suitable metals.

In general, the synthesis of complexes of general Formula IV [M(NPR$_3$)X$_{(m-1)}$]$_n$ requires a M to R$_3$PN$^-$ ratio of 1:1 or greater. The suitable ratio of the metal salt to M'(NPR$_3$)$_b$ varies with the specific metal, leaving group (X) and M'(NPR$_3$)$_b$ reagent. When b=1 or when a [Mg(NPR$_3$)X] reagent is used, the ratio of the metal salt to M'(NPR$_3$)$_b$ used for this synthesis can be about a 1:1 ratio; however, yields are generally higher in the presence of an excess of the metal salt. For example, a ratio of 2:1 may be suitable. When b=2, the excess of metal salt is maintained in the range from 2:1 to 4:1 to ensure that the M to R3PN$^-$ ratio in the product is 1:1 or greater.

The anionic metathesis can be conducted in low to ambient temperatures. For example, temperatures may range from −80 to 25° C. when the reaction is carried out in an inert organic solvent. The anionic metathesis reaction is preferably conducted at a temperature in the range from −75 to −35° C., as demonstrated in the synthesis of [Co(NP$^t$Bu$_3$)]$_4$ and [Ni(NP$^t$Bu$_3$)]$_4$ described herein.

The catalysts of Formula II and III of the present disclosure, whether purified or in situ-derived, can be used for the C—O bond hydrogenolysis of a range of organic substrates having at least one carbon-oxygen bond. The present disclosure exemplifies substrates that model the oxygen-containing functionality and structural types typically found in biomass feedstocks.

Furthermore, the low oxidation state of the metal centers in these catalysts make them amenable to oxidative passivation. For example, the catalysts can be treated by a oxygen reagent, such as O$_2$, to prepare air-stable oxidized catalyst derivatives. Transition metal oxides are industrially useful precatalysts for hydrogenation and hydrotreatment.

As a person skilled in the art would appreciate, the class of organic oxygen-containing substrates that can be reductively cleaved using the catalysts described herein is very broad. The substituents present on the substrates can be aliphatic, aromatic, unsaturated, contain heteroatoms, be cyclic or linear, possess functional groups, or contain a combination of these features. The common feature underlying these substrates is that they contain at least one carbon-oxygen bond, and the common underlying transformation is that the carbon-oxygen bond is transformed into a carbon-hydrogen bond.

The present disclosure exemplifies the C—O bond hydrogenolysis of different classes of oxygen-containing organic substrates. An embodiment relates to the C—O bond hydrogenolysis of dibenzofuran and dibenzofuran derivatives. The reaction conditions employed in this process are similar to those described above for General Reaction 1 in relation to the catalyst of Formula II (i.e. [MNPR$_3$]$_i$). The oxygen-containing substrate can be represented by the following formula:

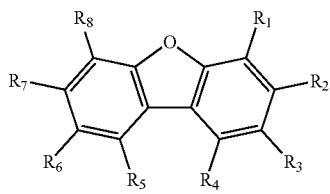

where:
R$^1$, R$^2$, R$^3$, R$^4$, R$^5$, R$^6$, R$^7$, R$^8$ can be the same group or different groups;
R$^1$, R$^2$, R$^3$, R$^4$, R$^5$, R$^6$, R$^7$, R$^8$ can be hydrogen, alkyl (C$_{1-18}$, primary, secondary and tertiary alkyl), cycloalkyl (C3-C8), aryl/heteroaryl, substituted aryl/heteroaryl or a functional group optionally containing at least one heteroatom;
any two vicinal R groups may also be linked to give cyclic systems, both aliphatic and aromatic [(e.g., R1/R2= —(CH$_2$)$_n$—, where n=3-10]; and
the term "heteroatom" refers to Group 15 and 16 elements, such as N, S and O. As noted, usable temperatures and pressures will vary as a function of the solvent used, the concentration of the components, the substrate, and the catalyst, among other factors. Similarly, the solvent will vary depending on the structure and properties (i.e., solubility) of the substrate, but can be determined by a person skilled in the art.

The catalysts of the present disclosure also reductively cleave furan derivatives. The reaction conditions employed in this process are similar to those described for the compounds of Formula I and II defined above in General Reactions 1 and 2. The substrate can be represented by the general formula:

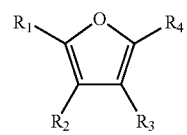

where:
R$^1$, R$^2$, R$^3$, R$^4$ can be the same group or different groups;
R$^1$, R$^2$, R$^3$, R$^4$ can be alkyl (C1-18, primary, secondary and tertiary alkyl), cycloalkyl (C3-C8), aryl/heteroaryl, substituted aryl/heteroaryl or a functional group optionally containing at least one heteroatom;
any two vicinal R groups may also be linked to give cyclic systems, both aliphatic and aromatic [(e.g., R1/R2= —(CH$_2$)$_n$—, where n=3-10]; and
the term "heteroatom" refers to Group 15 and 16 elements, such as N, S and O.

The catalysts of the present disclosure also reductively cleave benzofuran and benzofuran derivatives. The reaction conditions employed in this process are similar to those described above for General Reactions 1 and 2. The substrate can be represented by the general formula:

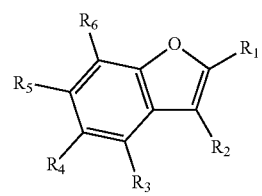

where:
R$^1$, R$^2$, R$^3$, R$^4$, R$^5$, R$^6$ can be the same group or different groups;
R$^1$, R$^2$, R$^3$, R$^4$, R$^5$, R$^6$ can be hydrogen, alkyl (C1-18, primary, secondary and tertiary alkyl), cycloalkyl (C3-C8), aryl/heteroaryl, substituted aryl/heteroaryl or a functional group optionally containing at least one heteroatom;
any two vicinal R groups may also be linked to give cyclic systems, both aliphatic and aromatic [(e.g., R1/R2= —(CH$_2$)$_n$—, where n=3-10]; and
the term "heteroatom" refers to Group 15 and 16 elements, such as N, S and O.

In another embodiment, the catalysts also reductively cleave ethers into hydrocarbons and/or alcohols. The reaction conditions employed in this process are similar to those described above for General Reactions 1 and 2. The substrate can be represented by the general formula:

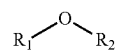

where:
R$^1$, R$^2$ can be the same group or different groups;
R$^1$, R$^2$ can be alkyl (C1-18, primary, secondary and tertiary alkyl), cycloalkyl (C3-C8), aryl/heteroaryl, substituted aryl/heteroaryl or a functional group optionally containing at least one heteroatom; and $R^1$ and $R^2$ may also be linked to give cyclic systems, both aliphatic and aromatic [(e.g., R1/R2=—(CH$_2$)$_n$—, where n=3-10]; and the term "heteroatom" are Group 15 and 16 elements, preferably N, S and O.

In a specific example, diphenyl ether can be reductively cleaved into a mixture of benzene and phenol. Prolonged reaction times result in a higher benzene to phenol ratio, suggesting that phenol, a substrate containing only one carbon-oxygen bond, is deoxygenated to produce benzene under the reaction conditions described in this disclosure.

$$2\ R-OH \xrightarrow{\substack{[M(NPR_3)]_n, \\ [H] \\ M'B}} 2\ R-H\ +\ M'_aO_b$$

In the case of diaryl ethers, the aromatic rings can be linked by a group E:

where:

E=alkyl, O, S, NR$^9$ $R^1, R^2, R^3, R^4, R^5, R^6, R^7, R^8, R^9$ can be the same group or different groups;

$R^1, R^2, R^3, R^4, R^5, R^6, R^7, R^8, R^9$ can be hydrogen, alkyl (C1-18, primary, secondary and tertiary alkyl), cycloalkyl (C3-C8), aryl/heteroaryl, substituted aryl/heteroaryl or a functional group optionally containing at least one heteroatom;

any two vicinal R groups may also be linked to give cyclic systems, both aliphatic and aromatic [(e.g., $R^1/R^2$=—(CH$_2$)$_n$—, where n=3-10]; and the term "heteroatom" refers to Group 15 and 16 elements, preferably N, S and O.

In another embodiment, the catalysts also deoxygenate substrates with carbon-oxygen double bonds into hydrocarbons. In this embodiment, the substrate with at least one carbon-oxygen double bond is preferably, but not necessarily, an unsaturated aldehyde or an unsaturated ketone. The reaction conditions employed in this process are similar to those described above for General Reactions 1 and 2 with silanes as the reducing agent. The substrate can be represented by the general formula:

where:

$R^1, R^2$ can be the same group or different groups;

$R^1, R^2$ can be alkyl (C1-18, primary, secondary and tertiary alkyl), cycloalkyl (C3-C8), aryl/heteroaryl, substituted aryl/heteroaryl or a functional group optionally containing at least one heteroatom; and $R^1, R^2$ can be alkyl or cycloalkyl containing unsaturated groups such as, but not limited to, carbon-carbon double bonds and carbon-carbon triple bonds;

$R^1$ and $R^2$ may also be linked to give cyclic systems, both aliphatic and aromatic [(e.g., R1/R2=—(CH$_2$)$_n$—, where n=3-10]; and the term "heteroatom" are Group 15 and 16 elements, preferably N, S and O.

The examples described in this disclosure include substrates of varying steric and electronic properties. In certain substrate classes, the specific substrates chosen represent the most sterically accessible and sterically hindered carbon-oxygen bonds. Substrates incorporating sterically hindered carbon-oxygen bonds are not typically known to be reductively cleaved by homogeneous transition metal catalysts. It should be apparent to a person skilled in the art that substrates containing carbon-oxygen bonds with steric accessibility intermediate to the provided range of examples can be reductively cleaved by the catalysts described herein. Furthermore, various substituents and degree of substitution are disclosed to illustrate, though not intended to limit, the variations in the electronic properties of the substrates that can be reductively cleaved by the catalysts described herein. The substituents presented as examples include some of the functional groups known present in oxygen-containing components of petroleum such as, but not limited to, alkyl, aromatic, heteroaromatic and alkoxy groups.

The non-limiting examples below serve to illustrate the embodiments described above.

EXAMPLES

In these examples, the following terms are used:
Ar—H=the hydrocarbon product.
Ar—OH=the alcohol product.
STOIC="Stoichiometric conversion" refers to experiments wherein no catalytic conversion was observed.

Example 1

Synthesis of [Ni(NP$^t$Bu$_3$)]$_4$

A nickel phosphoranimide catalyst having the formula shown below is synthesized as an example:

To prepare this catalyst (also referred to as the "Ni(I) catalyst"), 1.62 mmol of (dme)NiBr$_2$ and 0.81 mmol LiNP$^t$Bu$_3$ are separately suspended in 5 mL portions of tetrahydrofuran (THF) in 15 mL screw-capped vials under an inert atmosphere, for example, in a nitrogen- or argon-filled drybox. Both suspensions are cooled to −35° C. in a dry-box freezer for an hour. The LiNP$^t$Bu$_3$ suspension is added drop-wise into the metal halide suspension with occasional stirring over a four-hour period with the temperature constant at −35° C. After the addition of the ligand, the reaction mixture is left in the freezer overnight. The solvent is removed in vacuo and the residue is washed with 4 mL portions of hexane thrice. The residue is dissolved in 7 mL THF, charged with 2.5 mmol of Na delivered using a 1% Na/Hg reagent and stirred overnight. The solvent is evaporated and the product is extracted with pentane and filtered through a plug of Celite. The solvent is removed. This reaction gave an 80% yield. The product precipitates as dark green prismatic crystals from a concentrated THF solution upon cooling to −35° C. The product is characterized by X-ray crystallography, magnetic susceptibility measurement by the Evan's method (Evans, D. F. J. J. Chem. Soc. 1959, 2003-2005, which is herein incorporated by reference) and elemental analysis (vide infra).

The calculated elemental composition of the Ni(I) catalyst is C, 52.41%; H, 9.90%; N, 5.09%. The determined elemental composition is C, 52.38%; H, 9.89%; N, 4.96%. Solution magnetic susceptibility experiments revealed that the Ni(I) catalyst is a 3.50-electron paramagnet ($\mu_{eff}$=4.40 $\mu_{Bo}$) at room temperature.

Example 2

Synthesis of [Co(NP$^t$Bu$_3$)]$_4$

A cobalt phosphoranimide catalyst (also referred to herein as the "Co(I) catalyst") having the formula shown below is synthesized as an example:

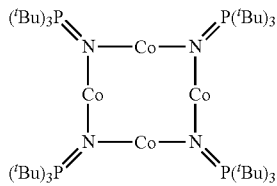

To prepare this catalyst, 1.62 mmol of CoCl$_2$ and 0.81 mmol LiNP$^t$Bu$_3$ are separately suspended in 5 mL portions of tetrahydrofuran (THF) in 15 mL screw-capped vials under an inert atmosphere, for example, in a nitrogen- or argon-filled drybox. Both suspensions are cooled to −35° C. in a dry-box freezer for an hour. The LiNP$^t$Bu$_3$ suspension is added dropwise into the metal halide suspension with occasional stirring over a four-hour period with the temperature constant at −35° C. After the addition of the ligand, the reaction mixture is left in the freezer overnight. The solvent is removed in vacuo and the residue is washed with 4 mL portions of hexane thrice. The residue is dissolved in 7 mL THF, charged with 2.5 mmol of Na delivered using a 1% Na/Hg reagent and stirred overnight. The solvent is evaporated and the product is extracted with pentane and filtered through a plug of Celite. The solvent is removed. This reaction gave a 65% yield. The product precipitates as prismatic dark brown crystals upon cooling to −35° C. The product is characterized by X-ray crystallography, magnetic susceptibility measurement by the Evan's method.

The calculated elemental composition is C, 52.36%; H, 9.89%; N, 5.09%. The determined elemental composition is C, 52.68%; H, 10.09%; N, 4.86%. The solution magnetic susceptibility experiments revealed that the Co(I) catalyst is an 8-electron paramagnet ($\mu_{eff}$=8.98 $\mu_{Bo}$) at room temperature.

Example 3

Synthesis of [Co(NP$^t$Bu$_3$)]$_4$ from [Cl$_2$Co$_2$(μ-NP$^t$Bu$_3$)$_2$(THF)$_2$]

All manipulations in this synthesis were carried out under inert atmosphere, for example, in a nitrogen- or argon-filled drybox. 0.5 mmol of [Cl$_2$Co$_2$(μ-NP-$^t$Bu$_3$)$_2$(THF)$_2$] is dissolved in 5 mL THF and then treated with 1.1 mmol Na(Hg) reagent at −35° C. to room temperature 12 hours. The solvent is evaporated and the product is extracted with pentane and filtered through a plug of Celite. The solvent is removed and a concentrated THF solution of the product is prepared for recrystallization. The product crystallizes as prismatic dark blue crystals upon cooling to −35° C. The product was identical in all respects to the cobalt(I) catalyst described above in Example 2.

Example 4

Synthesis of [Fe(NP$^t$Bu$_3$)]$_n$

An iron phosphoranimide catalyst having the formula [Fe(NP$^t$Bu$_3$)]$_n$ was synthesized.

To prepare this catalyst, 1.62 mmol of (dme)FeBr$_2$ and 0.81 mmol LiNP$^t$Bu$_3$ are separately suspended in 5 mL portions of tetrahydrofuran (THF) in 15 mL screw-capped vials under an inert atmosphere, for example, in a nitrogen- or argon-filled drybox. Both suspensions are cooled to −35° C. in a dry-box freezer for an hour. The LiNP$^t$Bu$_3$ suspension is added dropwise into the metal halide suspension with occasional stirring over a four-hour period with the temperature constant at −35° C. After the addition of the ligand, the reaction mixture is left in the freezer overnight. The solvent is removed in vacuo and the residue is washed with 4 mL portions of hexane thrice. The residue is dissolved in 7 mL THF, charged with 2.5 mmol of Na delivered using a 1% Na/Hg reagent and stirred overnight. The solvent is evaporated and the product is extracted with pentane and filtered through a plug of Celite. The solvent is removed. This reaction forms an amorphous dark brown solid in 50% yield.

Example 5

Stoichiometric Hydrodeoxygenation of Styrene Oxide

The preparation of reaction mixtures is conducted under an inert atmosphere, for example, in a nitrogen-filled dry box. 50 mg (0.41 mmol) styrene oxide, 95 mg (0.82 mmol) Et$_3$SiH and 20 mg (0.018 mmol) of the catalyst [Ni(NP$^t$Bu$_3$)]$_4$ are dissolved in 6 mL toluene. The solution is transferred into a Teflon-sealed glass reactor equipped with a Teflon-sealed magnetic stir bar. The reaction mixture is then stirred at 1200 rotations per minute (rpm) for 12 hours in an oil bath at 90° C.

The reactor is cooled to room and quenched with a 10% HCl solution. The organic products are extracted through diethyl ether-water extractions using three 4 mL portions of diethyl ether. The diethyl ether fractions are pooled, dried with anhydrous Na$_2$SO$_4$ and filtered through a small column of Florisil. The diethyl ether is removed in vacuo and the residue is dissolved in CDCl$_3$ for $^1$H-NMR and GC-MS analyses. Stoichiometric (STOIC) conversion to styrene is observed, in the absence of an efficient scavenger for H$_2$O.

Example 6

Stoichiometric Hydrodeoxygenation of Cyclododecene Oxide

The preparation of reaction mixtures is conducted under an inert atmosphere, for example, in a nitrogen-filled dry box. 70 mg (0.38 mmol) styrene oxide, 88 mg (0.76 mmol) Et$_3$SiH and 20 mg (0.018 mmol) of the catalyst [Ni(NP$^t$Bu$_3$)]$_4$ are dissolved in 6 mL toluene. The solution is transferred into a Teflon-sealed glass reactor equipped with a Teflon-sealed magnetic stir bar. The reaction mixture is then stirred at 1200 rotations per minute (rpm) for 12 hours in an oil bath at 90° C.

The reactor is cooled to room and quenched with a 10% HCl solution. The organic products are extracted through diethyl ether-water extractions using three 4 mL portions of diethyl ether. The diethyl ether fractions are pooled, dried with anhydrous $Na_2SO_4$ and filtered through a small column of Florisil. The diethyl ether is removed in vacuo and the residue is dissolved in $CDCl_3$ for $^1H$-NMR and GC-MS analyses. Stoichiometric (STOIC) conversion to cyclododecene, exclusively, is observed, in the absence of a competitive scavenger for $H_2O$.

Example 7

Catalytic C—O Bond Hydrogenolysis of Diphenyl Ether

The preparation of reaction mixtures is conducted under an inert atmosphere, for example, in a nitrogen-filled dry box. A Teflon-sealed reactor is charged with 100 mg (0.58 mmol) diphenyl ether, 40 mg (0.036 mmol) $[Ni(NP^tBu_3)]_4$, 126 mg (1.16 mmol) LDA, 6 mL toluene and a Teflon-sealed magnetic stir bar. The reactor was taken out of the dry box and connected to a hydrogen manifold. The reaction vessel is then charged with $H_2$ (1 atm), employing rigorous inert-atmosphere laboratory techniques. The reaction mixture is then stirred at 1200 rpm for 16 hours in an oil bath at 120° C.

The reactor is cooled to room and the reaction mixture quenched with a 10% HCl solution. The organic products are extracted through diethyl ether-water extractions using three 2 mL portions of diethyl ether. The diethyl ether fractions are pooled and subjected to GC-MS analyses. A 20% conversion of the substrate to a mixture of phenol and benzene was observed.

Example 8

Catalytic C—O Bond Hydrogenolysis of 4-methoxybiphenyl

The preparation of reaction mixtures is conducted under an inert atmosphere, for example, in a nitrogen-filled dry box. A Teflon-sealed reactor is charged with 100 mg (0.54 mmol) 4-methoxybiphenyl, 40 mg (0.036 mmol) $[Ni(NP^tBu_3)]_4$, 126 mg (1.16 mmol) LDA, 6 mL toluene and a Teflon-sealed magnetic stir bar. The reactor was taken out of the dry box and connected to a hydrogen manifold. The reaction vessel is then charged with $H_2$ (1 atm), employing rigorous inert-atmosphere laboratory techniques. The reaction mixture is then stirred at 1200 rpm for 16 hours in an oil bath at 130° C.

The reactor is cooled to room and the reaction mixture quenched with a 10% HCl solution. The organic products are extracted through diethyl ether-water extractions using three 2 mL portions of diethyl ether. The diethyl ether fractions are pooled and subjected to GC-MS analyses. A 24% conversion of the substrate to biphenyl was observed.

Example 9

Catalytic C—O Bond Hydrogenolysis of 4-Methoxybiphenyl in the Presence of Silane The preparation of reaction mixtures is conducted under an inert atmosphere, for example, in a nitrogen-filled dry box. 50 mg (0.27 mmol) 4-methoxybiphenyl, 59 mg (0.82 mmol) $PhSiH_3$ and 20 mg (0.018 mmol) of the catalyst $[Ni(NP^tBu_3)]_4$ are dissolved in 6 mL toluene. The solution is transferred into a Teflon-sealed glass reactor equipped with a Teflon-sealed magnetic stir bar. The reaction mixture is then stirred at 1200 rotations per minute (rpm) for 36 hours in an oil bath at 150° C.

The reactor is cooled to room and quenched with a 10% HCl solution. The organic products are extracted through diethyl ether-water extractions using three 4 mL portions of diethyl ether. The diethyl ether fractions are pooled, dried with anhydrous $Na_2SO_4$ and filtered through a small column of Florisil. The diethyl ether is removed in vacuo and the residue is dissolved in $CDCl_3$ for $^1H$-NMR and GC-MS analyses. A conversion of 48% to biphenyl was observed.

Example 10

Catalytic C—O Bond Hydrogenolysis of 4-Methoxybiphenyl (4-MBP) Using Hydrogen in the Presence of a Basic Scavenger This is a general procedure employed in the examples for the hydrogenolysis of 4-methoxybiphenyl under varying pressure and temperature conditions, as shown below.

The preparation of reaction mixtures is conducted under an inert atmosphere, for example, in an Argon or nitrogen drybox. The desired amount of substrate, catalyst and basic scavenger, as indicated in Table 1, are mixed in toluene (5 to 10 mL). The mixture is transferred into the appropriate pressure reactor equipped with a Teflon magnetic stir bar. C—O hydrogenolysis reaction examples run under hydrogen pressures lower than 2 atm are carried out in medium-walled glass pressure reactors, while processes employing pressures higher than 2 atm are contained in a glass-lined steel autoclave. The reaction vessels are charged with $H_2$, employing strict inert-atmosphere laboratory techniques, and heated to the desired temperature in an oil bath on a heating magnetic stir plate, stirring at 1200 rpm.

After the desired reaction time, the reaction mixture is cooled to room temperature and then quenched with a 10% HCl solution. The organic products are extracted through a series of diethyl ether-water extractions and the organic fractions are pooled, dried with anhydrous $Na_2SO_4$ and filtered through a small column of Florisil. The solvent is removed in vacuo and the weighed residue is dissolved in $CDCl_3$ for $^1H$-NMR and GC-MS analyses. The percentage recovery (yield) of hydrogenolysis products is determined by conducting experiments that have been allowed to proceed to completion.

Hydrogen pressures and temperatures employed in these reactions can vary over considerable range, which would be apparent to a person skilled in the art, based upon the teachings of this disclosure and the common general knowledge in the field of chemical catalysis.

Table 1 shows some examples of $[Ni(NP^tBu_3)]_4$- and $[Co(NP^tBu_3)]_4$)-catalyzed hydrogenolysis of 4-methoxybiphenyl (4-MBP) and the corresponding process conditions employed. The examples are conducted using the general procedure described in Example 10. Examples that proceeded to completion, exemplified by entry 2, gave an isolated yield of 95%.

TABLE 1

Summary of hydrogenolysis of 4-methoxybiphenyl in toluene.

| | (4-MBP) | | Cat | KH | Temp | Time | % Conversion | |
|---|---|---|---|---|---|---|---|---|
| Entry | mg (mmol) | Cat | mg (mmol) | mg (mmol) | (° C.) | (h) | Ar—H | Ar—OH |
| 1 | 45 (0.24) | [Ni(NP$^t$Bu$_3$)]$_4$ | 15 (0.013) | 29 (0.73) | 110 | 15 | 18 | 1 |
| 2 | 45 (0.24) | [Ni(NP$^t$Bu$_3$)]$_4$ | 15 (0.013) | 29 (0.73) | 120 | 36 | 50 | 50 |
| 3 | 95 (0.52) | [Ni(NP$^t$Bu$_3$)]$_4$ | 9 (0.008) | 62 (1.55) | 120 | 15 | 12 | 31 |
| 4 | 100 (0.54) | [Co(NP$^t$Bu$_3$)]$_4$ | 9 (0.008) | 65 (1.63) | 120 | 14 | 6 | 7 |

Example 11

Catalytic C—O Bond Hydrogenolysis of 2-Methoxynaphthalene (2-MN) in the Presence of a Basic Scavenger This is a general procedure employed in the examples for the hydrogenolysis of 2-methoxynaphthalene under varying pressure and temperature conditions, as shown below.

The preparation of reaction mixtures is conducted under an inert atmosphere, for example, in an Argon or nitrogen drybox. The desired amount of substrate, catalyst and basic scavenger, as indicated in Table 2, are mixed in toluene (5 to 10 mL). The mixture is transferred into the appropriate pressure reactor equipped with a Teflon magnetic stir bar. C—O hydrogenolysis reaction examples run under hydrogen pressures lower than 2 atm are carried out in medium-walled glass pressure reactors, while processes employing pressures higher than 2 atm are contained in a glass-lined steel autoclave. The reaction vessels are charged with H$_2$, employing strict inert-atmosphere laboratory techniques, and heated to the desired temperature in an oil bath on a heating magnetic stir plate, stirring at 1200 rpm.

After the desired reaction time, the reaction mixture is cooled to room temperature and then quenched with a 10% HCl solution. The organic products are extracted through a series of diethyl ether-water extractions and the organic fractions are pooled, dried with anhydrous Na$_2$SO$_4$ and filtered through a small column of Florisil. The solvent is removed in vacuo and the weighed residue is dissolved in CDCl$_3$ for $^1$H-NMR and GC-MS analyses. The percentage recovery (yield) of hydrogenolysis products is determined by conducting experiments that have been allowed to proceed to completion.

Hydrogen pressures and temperatures employed in these reactions can vary over considerable range, which would be apparent to a person skilled in the art, based upon the teachings of this disclosure and the common general knowledge in the field of chemical catalysis.

Table 2 shows two examples of [Ni(NP$^t$Bu$_3$)]$_4$- and [Co(NP$^t$Bu$_3$)]$_4$)-catalyzed hydrogenolysis of 4-methoxybiphenyl (4-MBP) and the corresponding process conditions employed. The examples are conducted using the general procedure described in Example 11. Examples that proceeded to completion, exemplified by entry 2, gave an isolated yield of 97%.

Example 12

Catalytic C—O Bond Hydrogenolysis of Benzyl Phenyl Ether

The preparation of reaction mixtures is conducted under an inert atmosphere, for example, in a nitrogen-filled dry box. A Teflon-sealed reactor is charged with 100 mg (0.54 mmol) benzyl phenyl ether, 13 mg (0.012 mmol) [Ni(NP$^t$Bu$_3$)]$_4$, 65 mg (1.62 mmol) KH, 6 mL toluene and a Teflon-sealed magnetic stir bar. The reactor was taken out of the dry box and connected to a hydrogen manifold. The reaction vessel is then charged with H$_2$ (1 atm), employing rigorous inert-atmosphere laboratory techniques. The reaction mixture is then stirred at 1200 rpm for 16 hours in an oil bath at 130° C.

The reactor is cooled to room and the reaction mixture quenched with a 10% HCl solution. The organic products are extracted through diethyl ether-water extractions using three 2 mL portions of diethyl ether. The diethyl ether fractions are pooled and subjected to GC-MS analyses. A 45% conversion of the substrate to phenol was observed and benzyl alcohol was not detected suggesting the catalyst selectivity for benzylic C—O bonds.

Example 13

Catalytic C—O Bond Hydrogenolysis of Diphenyl Ether

The preparation of reaction mixtures is conducted under an inert atmosphere, for example, in a nitrogen-filled dry box. A Teflon-sealed reactor is charged with 100 mg (0.58 mmol) diphenyl ether, 11 mg (0.010 mmol) [Ni(NP$^t$Bu$_3$)]$_4$, 70 mg (1.74 mmol) KH, 6 mL toluene and a Teflon-sealed magnetic stir bar. The reactor was taken out of the dry box and connected to a hydrogen manifold. The reaction vessel is then charged with H$_2$ (1 atm), employing rigorous inert-atmosphere laboratory techniques. The reaction mixture is then stirred at 1200 rpm for 16 hours in an oil bath at 120° C.

The reactor is cooled to room and the reaction mixture quenched with a 10% HCl solution. The organic products are extracted through diethyl ether-water extractions using three 2 mL portions of diethyl ether. The diethyl ether fractions are

TABLE 2

Summary of hydrogenolysis of 2-methoxynaphthalene catalyzed by [Ni(NP$^t$Bu$_3$)]$_4$ in toluene

| | (4-MN) | Cat | KH | Temp | Time | % Conversion | |
|---|---|---|---|---|---|---|---|
| Entry | mg (mmol) | mg (mmol) | mg (mmol) | (° C.) | (h) | Ar—H | Ar—OH |
| 1 | 85 (0.54) | 8 (0.007) | 64 (1.61) | 110 | 17 | 22 | 10 |
| 2 | 85 (0.54) | 10 (0.009) | 64 (1.61) | 120 | 21 | 68 | 32 | pooled and subjected to GC-MS analyses. Complete conversion of the substrate to a 3:1 benzene-phenol mixture was observed. This suggests that the catalyst can deoxygenate phenol to benzene, as well as cleave the aryl ether C—O linkage.

Example 14

Catalytic C—O Bond Hydrogenolysis of 1,3-Bis(4-Methoxyphenoxy)Benzene

The preparation of reaction mixtures is conducted under an inert atmosphere, for example, in a nitrogen-filled dry box. A Teflon-sealed reactor is charged with 130 mg (0.40 mmol) 1,3-bis(4-methoxyphenoxy)benzene, 14 mg (0.013 mmol) [Ni(NP$^t$Bu$_3$)]$_4$, 97 mg (2.42 mmol) KH, 6 mL toluene and a Teflon-sealed magnetic stir bar. The reactor was taken out of the dry box and connected to a hydrogen manifold. The reaction vessel is then charged with H$_2$ (1 atm), employing rigorous inert-atmosphere laboratory techniques. The reaction mixture is then stirred at 1200 rpm for 16 hours in an oil bath at 130° C.

The reactor is cooled to room and the reaction mixture quenched with a 10% HCl solution. The organic products are extracted through diethyl ether-water extractions using three 2 mL portions of diethyl ether. The diethyl ether fractions are pooled and subjected to GC-MS analyses. A quantitative mixture of the following composition was obtained:

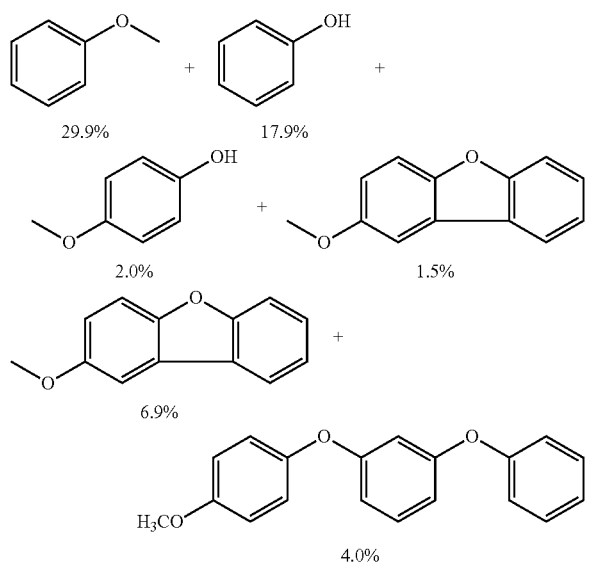

*The remaining 38% of the mixture obtained is recovered starting material.

The observed product distribution suggests that the catalysts can be used for reductive depolymerization of polymeric ethers without competitive aromatic hydrogenation.

Example 15

Catalytic Hydrodeoxygenation of 1,2-Diphenylisobenzofuran

The preparation of reaction mixtures is conducted under an inert atmosphere, for example, in a nitrogen-filled dry box. A Teflon-sealed reactor is charged with 100 mg (0.37 mmol) diphenylisobenzofuran, 10 mg (0.009 mmol) [Ni(NP$^t$Bu$_3$)]$_4$, 44 mg (1.10 mmol) KH, 6 mL toluene and a Teflon-sealed magnetic stir bar. The reactor was taken out of the dry box and connected to a hydrogen manifold. The reaction vessel is then charged with H$_2$ (1 atm), employing rigorous inert-atmosphere laboratory techniques. The reaction mixture is then stirred at 1200 rpm for 16 hours in an oil bath at 120° C.

The reactor is cooled to room and the reaction mixture quenched with a 10% HCl solution. The organic products are extracted through diethyl ether-water extractions using three 2 mL portions of diethyl ether. The diethyl ether fractions are pooled and subjected to GC-MS analyses. A 95% conversion of the substrate to 1,2-dibenzylbenzene, the completely deoxygenated product, was observed.

Example 16

Catalytic Hydrodeoxygenation of Dibenzofuran (DBF)

This is a general procedure employed in the examples for the hydrodeoxygenation of dibenzofuran under varying pressure and temperature conditions, as shown below.

The preparation of reaction mixtures is conducted under an inert atmosphere, for example, in an Argon or nitrogen drybox. The desired amount of substrate, catalyst and basic scavenger, as indicated in Table 3, are mixed in toluene (5 to 10 mL). The mixture is transferred into the appropriate pressure reactor equipped with a Teflon magnetic stir bar. C—O hydrogenolysis reaction examples run under hydrogen pressures lower than 2 atm are carried out in medium-walled glass pressure reactors, while processes employing pressures higher than 2 atm are contained in a glass-lined steel autoclave. The reaction vessels are charged with H$_2$, employing strict inert-atmosphere laboratory techniques, and heated to the desired temperature in an oil bath on a heating magnetic stir plate, stirring at 1200 rpm.

After the desired reaction time, the reaction mixture is cooled to room temperature and then quenched with a 10% HCl solution. The organic products are extracted through a series of diethyl ether-water extractions and the organic fractions are pooled, dried with anhydrous Na$_2$SO$_4$ and filtered through a small column of Florisil. The solvent is removed in vacuo and the weighed residue is dissolved in CDCl$_3$ for $^1$H-NMR and GC-MS analyses. The percentage recovery (yield) of hydrodeoxygenation products is determined by conducting experiments that have been allowed to proceed to completion.

Hydrogen pressures and temperatures employed in these reactions can vary over considerable range, which would be apparent to a person skilled in the art, based upon the teachings of this disclosure and the common general knowledge in the field of chemical catalysis.

Table 3 shows some examples of [Ni(NP$^t$Bu$_3$)]$_4$- and [Co(NP$^t$Bu$_3$)]$_4$)-catalyzed hydrodeoxygenation of DBF and the corresponding process conditions employed. The examples are conducted using the general procedure described in Example 16. Examples that proceeded to completion, exemplified in all entries, gave an isolated yield of 95 to 97%.

TABLE 3

Summary of HDO experiments of DBF catalyzed by [Ni(NP$^t$Bu$_3$)]$_4$ in toluene

| Entry | DBF mg (mmol) | Cat mg (mmol) | KH mg (mmol) | Temp (°C.) | Time (h) | % Conversion Ar—OH | Ar—H |
|---|---|---|---|---|---|---|---|
| 1 | 62 (0.37) | 10 (0.009) | 30 (0.74) | 120 | 18 | 100 | 0 |
| 2 | 43 (0.26) | 8 (0.007) | 20 (0.50) | 130 | 18 | 100 | 0 |
| 3 | 76 (0.45) | 8 (0.007) | 36 (0.90) | 135 | 18 | 100 | 0 |
| 4 | 200 (1.18) | 7 (0.006) | 95 (2.38) | 150 | 18 | 96 | 4 |
| 5 | 200 (1.18) | 7 (0.006) | 95 (2.38) | 180 | 0.8 | 20 | 1 |

Example 17

Catalytic Hydrodeoxygenation of Dibenzofuran in the Presence of an Lewis Acids

This is a general procedure employed in the examples for the hydrodeoxygenation of dibenzofuran in the presence of Lewis Acid additives, as shown below.

The preparation of reaction mixtures is conducted under an inert atmosphere, for example, in an Argon or nitrogen drybox. The desired amount of substrate, catalyst, Lewis acid additive and basic scavenger, as indicated in Table 4, are mixed in toluene (5 to 10 mL). The mixture is transferred into the appropriate pressure reactor equipped with a Teflon magnetic stir bar. C—O hydrogenolysis reaction examples run under hydrogen pressures lower than 2 atm are carried out in medium-walled glass pressure reactors, while processes employing pressures higher than 2 atm are contained in a glass-lined steel autoclave. The reaction vessels are charged with H$_2$, employing strict inert-atmosphere laboratory techniques, and heated to the desired temperature in an oil bath on a heating magnetic stir plate, stirring at 1200 rpm.

After the desired reaction time, the reaction mixture is cooled to room temperature and then quenched with a 10% HCl solution. The organic products are extracted through a series of diethyl ether-water extractions and the organic fractions are pooled, dried with anhydrous Na$_2$SO$_4$ and filtered through a small column of Florisil. The solvent is removed in vacuo and the weighed residue is dissolved in CDCl$_3$ for $^1$H-NMR and GC-MS analyses. The percentage recovery (yield) of hydrodeoxygenation products is determined by conducting experiments that have been allowed to proceed to completion.

Hydrogen pressures and temperatures employed in these reactions can vary over considerable range, which would be apparent to a person skilled in the art, based upon the teachings of this disclosure and the common general knowledge in the field of chemical catalysis.

Table 4 shows some examples of [Ni(NP$^t$Bu$_3$)]$_4$-catalyzed hydrodeoxygenation of DBF in the presence of Lewis acid additives and the corresponding process conditions employed. The examples are conducted using the general procedure described in Example 17. Examples that proceeded to completion, exemplified in all entries, gave an isolated yield of 95 to 97%.

TABLE 4

Summary of HDO experiments of DBF catalyzed by [Ni(NP$^t$Bu$_3$)]$_4$ in the presence of trialkylaluminum additives at 150° C.

| Entry | DBF mg (mmol) | Cat mg (mmol) | KH mg (mmol) | Additive | mg (mmol) | Time (h) | % Conversion Ar—OH | Ar—H |
|---|---|---|---|---|---|---|---|---|
| 1 | 250 (1.49) | 5 (0.004) | 120 (3.0) | AlMe$_3$ | 50 (0.70) | 12 | 10 | 90 |
| 2 | 250 (1.49) | 5 (0.004) | 120 (3.0) | Al$^i$Bu$_3$ | 138 (0.70) | 12 | 80 | 20 |

Example 18

Catalytic Deoxygenation of Carvone

A 100 mL Teflon-sealing glass reactor equipped with a Teflon-covered magnetic stir bar was charged with 8 mg (0.007 mmol) [NiNP$^t$Bu$_3$]$_4$, 100 mg (0.67 mmol) R-carvone, 73 mg (0.67 mmol) PhSiH$_3$ and 1.5 mL tetrahydrofuran (THF). The reaction mixture was allowed to stir at a speed of 1200 rpm for 16 hours at 60° C. temperature. The reaction mixture was then filtered through a plug of Florisil and the THF-fraction was subjected to GC-MS analysis. The substrate was completely converted into a mixture of products identified to be the following:

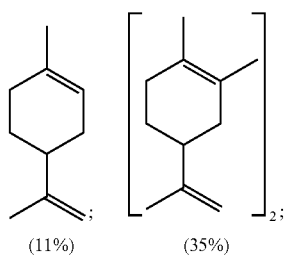

and the remaining fraction is a mixture of C=O hydrosilylation products.

Example 19

Catalytic Deoxygenation of 4-Ethylacetophenone (4-EAP)

A 100 mL Teflon-sealing glass reactor equipped with a Teflon-covered magnetic stir bar was charged with 8 mg (0.007 mmol) [NiNP$^t$Bu$_3$]$_4$, 100 mg (0.67 mmol) 4-ethylacetophenone, 73 mg (0.67 mmol) PhSiH$_3$ and 1.5 mL tetrahydrofuran (THF). The reaction mixture was allowed to stir at a speed of 1200 rpm for 16 hours at 60° C. temperature. The reaction mixture was then filtered through a plug of Florisil and the THF-fraction was subjected to GC-MS analysis. The following products were obtained:

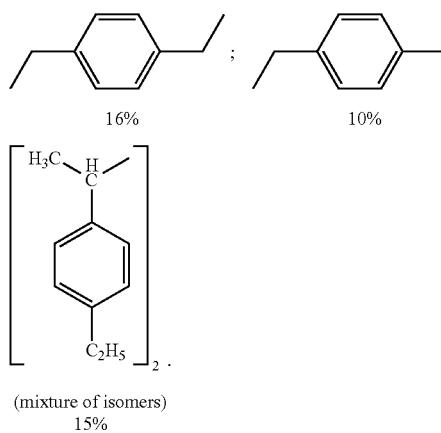

Example 20

Catalytic Deoxygenation of 3,4-diphenyl-2-cyclopentenone (3,4-DCP)

A 100 mL Teflon-sealing glass reactor equipped with a Teflon-covered magnetic stir bar was charged with the catalyst [NiNP$^t$Bu$_3$]$_4$, 3,4-diphenyl-2-cyclopentenone, PhSiH$_3$ and 1.5 mL tetrahydrofuran (THF) as indicated in Table 5. The reaction mixture was allowed to stir at a speed of 1200 rpm for 16 hours at 60° C. temperature. The reaction mixture was then filtered through a plug of Florisil and the THF-fraction was subjected to GC-MS analysis. A summary of results is provided in Table 7.

TABLE 5

Summary of HDO experiments of (3,4-DCP) catalyzed by [Ni(NP$^t$Bu$_3$)]$_4$ in THF

| Entry | (3,4-DCP) mg (mmol) | Cat mg (mmol) | PhSiH$_3$ mg (mmol) | Temp (° C.) | Time (h) | % Conversion |
|---|---|---|---|---|---|---|
| 1 | 100 (0.43) | 10 (0.009) | 47 (0.43) | 60 | 16 | 44 |
| 2 | 100 (0.43) | 10 (0.009) | 94 (0.86) | 60 | 16 | 100 |

Table 6 shows the product distribution for each entry in Table 5.

TABLE 6

Distribution of Reduction Products.

| Entry | % in the product mixture | | |
|---|---|---|---|
| | (cyclopentanone, 3,4-diphenyl) | (3,4-diphenylcyclopentene) | (diphenylcyclopentadiene and isomers) |
| 1 | 41 | 44 | 0 |
| 2 | 0 | 48 | 52 |

The invention claimed is:

1. A method of catalyzing a C—O bond hydrogenolysis reaction comprising:
reacting an organic substrate having at least one carbon-oxygen bond with a reducing agent and catalyst of general formula:

[M(NPR$_3$)]$_n$ where:
M is Fe, Co, Cu or Ni;
n is a whole number of at least 2;
the ratio of M to R$_3$PN$^-$ is 1:1;
R$_3$PN$^-$ is a monoanioinic phosphoranimide ligand of structure:

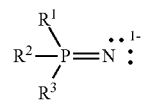

where:
R$^1$, R$^2$, R$^3$ are independently alkyl (C1-18, primary, secondary or tertiary alkyl), cycloalkyl (C3-C8) unsubstituted or alkyl-substituted, aryl/heteroaryl, substituted aryl/heteroaryl or an inert functional group containing at least one heteroatom; and
R$^1$, R$^2$, R$^3$ may be linked to give cyclic systems.

2. The method of claim 1, wherein R$^1$, R$^2$, R$^3$ are independently alkyl groups selected from the group consisting of methyl, ethyl, n-propyl, isopropyl, sec-butyl and t-butyl.

3. The method of claim 2, wherein R$^1$, R$^2$, R$^3$ are t-butyl.

4. The method of claim 1, wherein R$^1$, R$^2$, R$^3$ are independently cycloalkyl groups selected from the group consisting of cyclopentyl, cyclohexyl, alkyl-substituted cyclopentyl and alkyl-substituted cyclohexyl.

5. The method of claim 4, wherein R$^1$, R$^2$, R$^3$ are independently cyclohexyl or cyclopentyl.

6. The method of claim 1, wherein R$^1$, R$^2$, R$^3$ are aryl groups independently selected from the group consisting of phenyl, tolyl, xylyl, naphthanyl and biphenyl.

7. The method of claim 1, wherein the substrate is a dibenzofuran, or a derivative thereof, having the general formula:

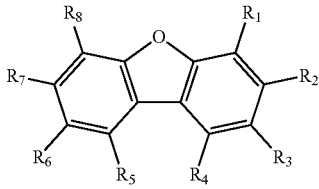

where:

R¹, R², R³, R⁴, R⁵, R⁶, R⁷, R⁸ are independently hydrogen, alkyl (C1-18, primary, secondary and tertiary alkyl), cycloalkyl (C3-C8), aryl/heteroaryl, substituted aryl/heteroaryl containing at least one heteroatom;

any two vicinal R groups may also be linked to give cyclic systems, both aliphatic and aromatic and the at least one heteroatom is selected from N, S and O.

8. The method of claim 1, wherein the substrate is a furan, or a derivative thereof, having the general formula:

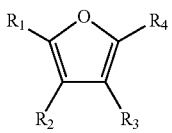

where:

R¹, R², R³, R⁴ are independently selected from hydrogen, alkyl (C1-18, primary, secondary and tertiary alkyl), cycloalkyl (C3-C8), aryl/heteroaryl, substituted aryl/heteroaryl wherein heteroatoms are selected from O, N and S, and wherein any two vicinal R groups may also be linked to give cyclic systems, both aliphatic and aromatic.

9. The method of claim 1, wherein the substrate is a benzofuran, or a derivative thereof, having the general formula:

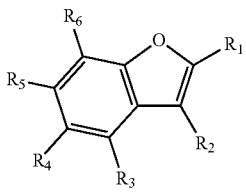

where:

R¹, R², R³, R⁴, R⁵, R⁶ are the same group or different groups selected from the group consisting of hydrogen, alkyl (C1-18, primary, secondary or tertiary alkyl), cycloalkyl (C3-C8), aryl/heteroaryl, substituted aryl/heteroaryl wherein heteroatoms are selected from the group consisting of O, N and S and wherein any two vicinal R groups may also be linked to give cyclic systems, both aliphatic and aromatic.

10. The method of claim 1, wherein the substrate is a diaryl ether where the aryl groups are connected, or a derivative, having the general formula:

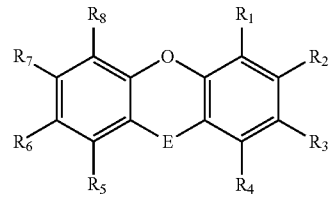

where:

E=O, S, NR⁹ or an alkyl group

R¹, R², R³, R⁴, R⁵, R⁶, R⁷, R⁸, R⁹ are the same group or different groups selected from the group consisting of hydrogen, alkyl (C1-18, primary, secondary or tertiary alkyl), cycloalkyl (C3-C8), aryl/heteroaryl, substituted aryl/heteroaryl wherein heteroatoms are selected from the group consisting of N, O and S; and wherein any two vicinal R groups may also be linked to give cyclic systems, both aliphatic and aromatic.

11. The method of claim 1, wherein the substrate is an ether, or a derivative thereof, having the general formula:

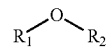

where:

R¹, R² can be the same group or different groups independently selected from the group consisting of alkyl (C1-18, primary, secondary or tertiary alkyl), cycloalkyl (C3-C8), aryl/heteroaryl, substituted aryl/heteroaryl wherein heteroatoms are selected from the group consisting of S, N and O; and R¹ and R² may also be linked to give cyclic systems, both aliphatic and aromatic.

12. The method of claim 1, wherein the substrate has a carbon oxygen double bond, or a derivative thereof, having the general formula:

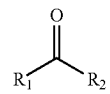

where:

R¹, R² are independently hydrogen, alkyl (C1-18, primary, secondary and tertiary alkyl), cycloalkyl (C3-C8), aryl/heteroaryl, substituted aryl/heteroaryl, wherein heteroatoms are selected from the group consisting of S, N and O; or alkyl containing unsaturated groups, or cycloalkyl containing unsaturated groups; or R¹ and R² are linked to give aliphatic or aromatic cyclic systems.

13. The method of claim 12, wherein the substrate is an unsaturated aldehyde or a ketone.

14. The method of claim 1, wherein the reacting is conducted under H₂ pressures of about 1 to 100 atm.

15. The method of claim 1, wherein the reacting is conducted at a temperature range of about 50 to 300° C.

16. The method of claim 1, wherein the reacting is done in the presence of an inert solvent selected from the group consisting of an alkyl solvent, an aromatic hydrocarbon solvent and an alkyl ether solvent.

17. The method of claim 1, wherein the reacting is carried out in the presence of a metal hydride, a metal amide, an alkyl halide or an aryl magnesium halide.

18. The method of claim 1, wherein the reacting is carried out in the presence of a trialkylaluminum additive to effect complete hydrodeoxygenation.

19. The method of claim 1, wherein the catalyst has been prepared in situ by the reaction below, and is used without purification in the reaction:

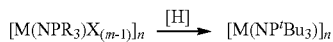

$$[M(NPR_3)X_{(m-1)}]_n \xrightarrow{[H]} [M(NP^tBu_3)]_n$$

where:
[M(NPR$_3$)X$_{(m-1)}$]$_n$ is a halide-functionalized metal-phosphoranimide complex where m=2 or 3;
n=2 to 4;
the M to R$_3$PN$^-$ ratio is 1:1;
M is a first row transition metal;
X$^-$ is a halide or pseudohalide;
R$_1$, R$_2$, R$^3$ are independently alkyl (C1-18, primary, secondary and tertiary alkyl), cycloalkyl (C3-C8), aryl/heteroaryl, substituted aryl/heteroaryl, wherein heteroatoms are selected from Si, N, S, and O; and
R$^1$, R$^2$, R$^3$ substituents may also be linked by aliphatic hydrocarbyl groups to give cyclic systems; and,
[H] is a reducing agent.

20. The method of claim 19, wherein X$^-$ is F$^-$, Cl$^-$, Br$^-$, I$^-$, or OSO$_2$R$^-$, where R=Me, Ph, p-Tol, or CF$_3$.

21. A method of catalyzing the C—O bond hydrogenolysis of an organic compound having at least one carbon-oxygen bond comprising:
reacting the organic substrate with a compound selected from the group consisting of [Fe(NP$^t$Bu$_3$)]$_4$, [Co(NP$^t$Bu$_3$)]$_4$ and [Ni(NP$^t$Bu$_3$)]$_4$.

22. The method of claim 21, wherein the substrate is selected from the group consisting of a dibenzofuran, benzofuran, furan, an ether, an aldehyde and a ketone.

23. A method of catalyzing the C—O bond hydrogenolysis of an organic substrate comprising:
reacting the organic substrate with a catalyst of Formula [M(NPR$_3$)]$_n$
wherein n is a whole number of at least 2;
the ratio of M to NPR$_3$ is 1:1;
M is a first row transition metal selected from the group consisting of Fe, Co and Ni;
NPR$_3$ is:

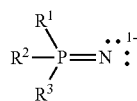

where:
R$^1$, R$^2$, R$^3$ are independently alkyl (C1-18, primary, secondary or tertiary alkyl), cycloalkyl (C3-C8), aryl/heteroaryl, substituted aryl/heteroaryl and heteroatoms are selected from Si, N, and O;
wherein R$^1$, R$^2$, R$^3$ may also be linked by aliphatic groups to give cyclic systems;
wherein the reaction is carried out at a temperature range of about 50 to 300° C. in the presence of a reducing agent selected from the group consisting of hydrogen and an organic silyl hydride; and
wherein the reaction is carried out in toluene or tetrahydrofuran.

24. A process for C—O bond hydrogenolysis of an organic substrate having at least one carbon-oxygen bond comprising:
(i) combining the organic substrate with a transition metal complex of Formula II and a reductant selected from hydrogen and an organic silyl hydride to obtain a reaction medium;
(ii) allowing the catalyst to catalyze the C—O bond hydrogenolysis of the substrate in an organic substrate selected from toluene and tetrahydrofuran;
(iii) obtaining the hydrogenolysis products derived from the organic substrate;
wherein the organic substrate is an aromatic or aliphatic compound containing at least one carbon-oxygen bond; and
wherein the complex of Formula II is:

[M(NPR$_3$)]$_n$     Formula II where
n is a whole number of at least 2;
the ratio of M to NPR$_3$ is 1:1;
M is a first row transition metal selected from the group consisting of Fe, Co and Ni;
NPR$_3$ is:

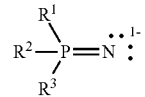

where:
R$^1$, R$^2$, R$^3$ are independently alkyl (C1-18, primary, secondary or tertiary alkyl), cycloalkyl (C3-C8), aryl/heteroaryl, substituted aryl/heteroaryl and heteroatoms are selected from the group consisting of Si, S, N, or O; and
wherein R$^1$, R$^2$, R$^3$ may also be linked by aliphatic groups to give cyclic systems.

* * * * *